(12) United States Patent
Tarler

(10) Patent No.: US 7,918,142 B1
(45) Date of Patent: *Apr. 5, 2011

(54) SENSOR FOR MEASURING SHEAR FORCES

(75) Inventor: Matthew David Tarler, Westlake, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 884 days.

This patent is subject to a terminal disclaimer.

(21) Appl. No.: 11/138,137

(22) Filed: May 26, 2005

Related U.S. Application Data

(63) Continuation of application No. 10/622,751, filed on Jul. 18, 2003, now Pat. No. 6,955,094.

(51) Int. Cl.
*G01N 3/24* (2006.01)
(52) U.S. Cl. .......................................... 73/841
(58) Field of Classification Search ............. 73/841
See application file for complete search history.

(56) References Cited

U.S. PATENT DOCUMENTS

| | | | | |
|---|---|---|---|---|
| 3,634,063 | A | * | 1/1972 | Hwang .............................. 75/345 |
| 4,349,339 | A | * | 9/1982 | Daniel ........................... 434/274 |
| 5,042,504 | A | * | 8/1991 | Huberti ......................... 600/592 |
| 5,313,840 | A | * | 5/1994 | Chen et al. ....................... 73/763 |
| 5,553,500 | A | * | 9/1996 | Grahn et al. .................... 73/628 |
| 5,571,973 | A | * | 11/1996 | Taylot ..................... 73/862.046 |
| 5,628,230 | A | * | 5/1997 | Flam ................................ 73/172 |
| 6,186,000 | B1 | * | 2/2001 | Kaneko et al. ................... 73/172 |
| 6,216,545 | B1 | * | 4/2001 | Taylor ...................... 73/862.046 |
| 2006/0137462 | A1 | * | 6/2006 | Divigalpitiya et al. .......... 73/760 |

OTHER PUBLICATIONS

"Rapid Prototyping helps Reebok stay on course." CAD/CAM Publishing, Inc. 2000.*
R. Hosein, M. Lord, "A study of in-shoe plantar shear in normals." Clinical Biomechanics 15 (2000) pp. 46-53.*
J. A. Paradiso, K. Hsiao, A. Y. Benbasat, Z. Teegarden, "Design and implementation of expressive footwear." IBM Systems Journal 39 (2000).*
R. E. Morley, Jr. E. J. Richter, J. W. Klaesner, K. S. Maluf, M. J. Mueller, "In-shoe multisensory data acquisition system." IEEE Transactions on Biomedical Engineering, vol. 48, No. 7 (Jul. 2001).*
F. Akhlaghi and M. G. Pepper, "In-shoe biaxial shear force measurement: the Kent shear system." Med. & Biol. Eng. & Comput., 34, pp. 315-317 (1996).*
K. Akasofu and M. R. Neuman, "A thin-film variable capacitance shear force sensor for medical and robotics applications." Annual International Conference of the IEEE Engineering in Medicine and Biology Society, vol. 13, No. 4 (1991).*
T. A. Chase and R. C. Luo, "A thin-film flexible capacitive tactile normal/shear force array sensor." IEEE Proceedings of the 1995 IEEE IECON 21$^{st}$ International Conference on, vol. 2.*
E. P. van der Putten and C. J. Snijders, "Shoe design for prevention of injuries in sport climbing." Applied Ergonomics, vol. 31, Issue 4. pp. 379-387 (Aug. 2001).*

(Continued)

*Primary Examiner* — Lisa M Caputo
*Assistant Examiner* — Punam Roy
(74) *Attorney, Agent, or Firm* — Brian M. Kolkowski

(57) ABSTRACT

The present invention is related to a sensor for simultaneously measuring both normal and shear forces applied to two or more flexible sensors, and further a statically responsive sensor for measuring shear forces. The present invention further includes a method of designing an object, prototype or a device using these sensors to detect both shear and normal forces encountered at the sensor locations.

29 Claims, 10 Drawing Sheets

OTHER PUBLICATIONS

D. Rosenbaum and H.-P. Becker, "Plantar pressure distribution measurements. Technical background and clinical applications." Foot and Ankle Surgery. 3: 1-14. (1997).*

"elastomer." Encyclopædia Britannica. 2009. Encyclopædia Britannica Online. Jun. 12, 2009 <http://www.britannica.corn/EBchecked/topic/182081/elastomers>.

Yi, et al., Property Balancing for Polyethylene-Based Carbon Black-Filled Conductive Composites, Journal of Applied Polymer Science, 1998, 131-138, vol. 67, John Wiley & Sons.

Hamza, The Role of Carbon Black on the Elastic Behaviour of EPDM/LDPE Blend, Materials Letters, 1997, 153-155, vol. 30, Elsevier Science.

* cited by examiner

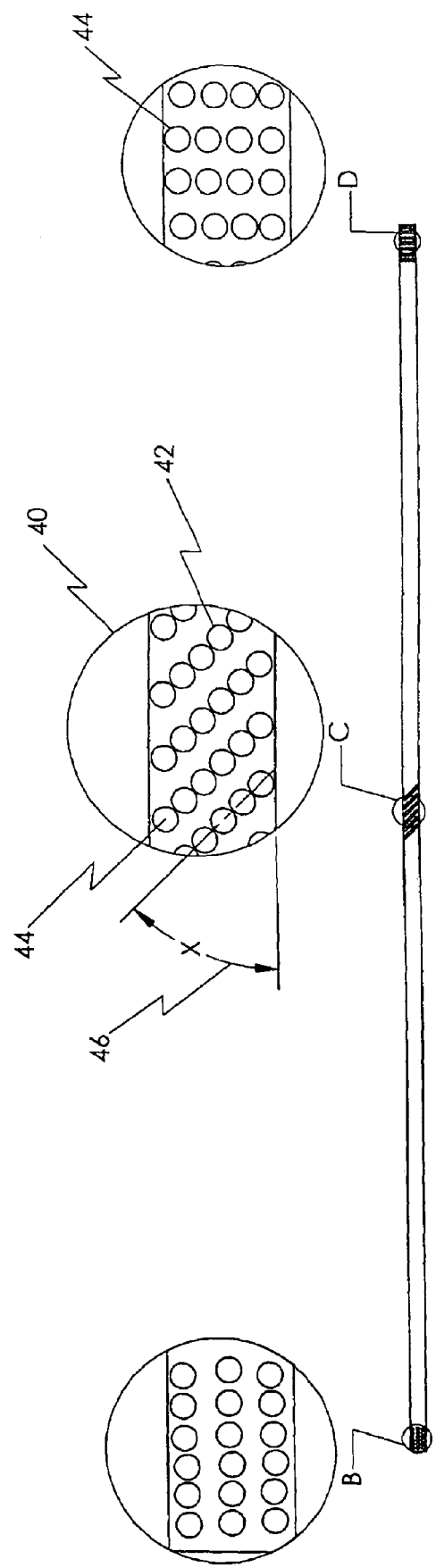

SENSOR FOR MEASURING SHEAR FORCES

CROSS-REFERENCE TO RELATED APPLICATIONS

This application is a continuation of U.S. patent application Ser. No. 10/622,751 with a filing date of Jul. 18, 2003 now U.S. Pat. No. 6,955,094.

The U.S. Government has a paid-up license in this invention and the right in limited circumstances to require the patent owner to license others on reasonable terms provided for by the terms of grant number 1R4341853-01 awarded by the National Institute of Health.

BACKGROUND OF THE INVENTION

1. Field of the Invention

The present invention is related to a sensor for simultaneously measuring both normal and shear forces applied to the sensor, and further a statically responsive sensor for measuring shear forces. The present invention further includes a method of designing an object or a device using these sensors.

2. Technical Background

The need for a thin, flexible shear force sensor has been apparent in multiple fields of discipline. The ability to measure shear forces is needed in many applications including prevention of pressure sores, neural prosthesis feedback and in prosthetic limbs. No product has been successfully engineered to replace the shear force sensors naturally found in our skin. These natural sensors provide vital information back to the brain for both safety and control applications. These safety concerns include the prevention of excessive shear forces, which have been correlated with the formation of pressure ulcers. The control applications include providing sensory feedback for both gross and fine motor control.

There are three somewhat crude sensors or techniques that have been developed to measure shear forces to date, but each of these sensors have their own limitations. The most common shear sensor currently produced is based on the principle of a strange gauge. The sensor is made out of metal and must be fixed to the object of interest. Even if this sensor was fabricated from a flexible material and bonded to the surface where lateral movement was being measured, which would be difficult, the basic principle of this type of sensor is to measure strain, and therefore tension or compression due to the surface becoming longer or shorter (e.g., in bending) and does not measure uniform shear stresses whereby the entire surface shifts equally with respect to the underlying material. Another type of shear sensor has been developed using piezoelectric transducers. These sensors are embedded with piezoelectric strips within a device, which is then dragged along a surface. As the piezoelectric device is dragged along a surface the piezoelectric sensors indicate changes in shear forces and therefore changes in the surface features. The piezoelectric device, however, does not have a static response and therefore can't be used to detect and measure the static shear forces that are of most concern. Finally, there are capacitive based sensors. These capacitive based sensors use relatively stiff sheet and metallic conductors that act as a mechanical low-pass filter, effectively distributing the force-induced strains among a number of adjacent sites.

The shear sensors outlined above are interesting, but are not applicable for measurement of the shear forces at all locations around a human body or in many other applications. A small flexible and compliant shear force sensor is still needed. It is an object of this invention to provide such a statically responsive shear sensor. It is a further object of this invention to provide a flexible sensor for simultaneously measuring both normal and shear forces. It is still a further object of this invention to provide a method of designing an object or device using these types of sensors.

SUMMARY OF THE INVENTION

The present invention is related to a sensor for simultaneously measuring both normal and shear forces applied to the sensor, and further a statically responsive sensor for measuring shear forces. The present invention further includes a method of designing an object or a device using these sensors.

In one embodiment, the present invention includes a sensor comprising two layers of contact material, and a flexible material interposed between the two layers of contact material; wherein the sensor can be used to simultaneously measure both shear and normal forces applied to the sensor.

In another embodiment, the present invention includes a sensor comprising at least two layers of contact material, and a flexible material interposed between the two layers of contact material; wherein at least one of the layers of contact material is formed from multiple conductive lines or regions, and the sensor can be used to simultaneously measure both shear and normal forces applied to the sensor.

In still another embodiment, the present invention includes a sensor comprising two layers of contact material, and a flexible material interposed between the two layers of contact material; wherein the sensor can be used to measure static shear forces applied to the sensor.

In still another embodiment, the present invention includes a sensor comprising at least two layers of contact material, and a flexible material interposed between the two layers of contact material; wherein at least one of the layers of contact material is formed from multiple conductive lines or regions, and the sensor can be used to measure static shear forces applied to the sensor.

In yet another embodiment, the present invention includes a method of designing an object or device comprising the steps of applying at least one flexible, compliant sensors capable of simultaneously measuring both shear and normal forces, to locations on a prototype design of an object or device being designed; using the prototype design with the applied sensors in at least one application or test over a test period of time; measuring both the shear and normal forces encountered at the sensor locations of the prototype design over at least part of the test time period; and modifying the design of the object or device in part based on the forces encountered by the prototype design during the application or test.

In yet still another embodiment, the present invention includes a method of designing an object or device comprising the steps of applying at least one flexible, compliant sensors capable of measuring static shear forces, to locations on a prototype design of an object or device being designed; using the prototype design with the applied sensors in at least one application or test over a test period of time; measuring the shear forces encountered at the sensor locations of the prototype design over at least part of the test time period; and modifying the design of the object or device in part based on the forces encountered by the prototype design during the application or test.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 3. Schematic representation of the composite material shown in FIG. 2 after the step of flattening of the composite material, and further schematic representation of the sub-sections of the composite material as shown in FIG. 2 after the step of flattening the composite material.

DESCRIPTION OF THE PREFERRED EMBODIMENT

Figure 1:
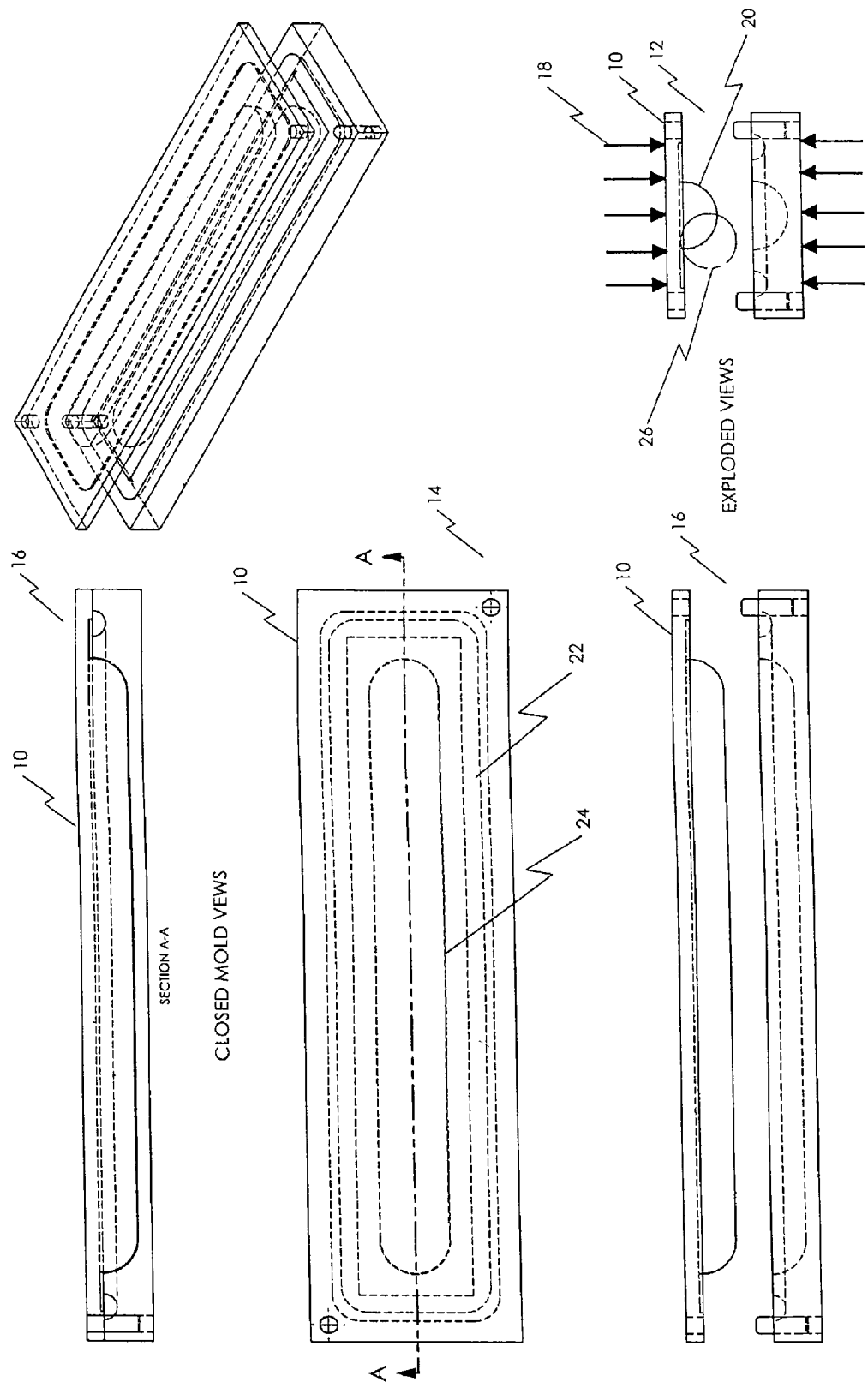
FIG. 1. Cross-sectional views of mold for molding composite material.

The present invention is related to a sensor for simultaneously measuring both normal and shear forces applied to the sensor, and further a statically responsive sensor for measuring shear forces. The present invention further includes a method of designing an object or a device using these sensors. The present invention encompasses numerous embodiments a number of which are set forth below.

In one embodiment, the present invention includes a sensor comprising two layers of contact material, and a flexible material interposed between the two layers of contact material; wherein the sensor can be used to simultaneously measure both shear and normal forces applied to the sensor.

In another embodiment, the present invention includes a sensor comprising at least two layers of contact material, and a flexible material interposed between the two layers of contact material; wherein at least one of the layers of contact material is formed from multiple conductive lines or regions, and the sensor can be used to simultaneously measure both shear and normal forces applied to the sensor.

In still another embodiment, the present invention includes a sensor comprising two layers of contact material, and a flexible material interposed between the two layers of contact material; wherein the sensor can be used to measure static shear forces applied to the sensor.

In still another embodiment, the present invention includes a sensor comprising at least two layers of contact material, and a flexible material interposed between the two layers of contact material; wherein at least one of the layers of contact material is formed from multiple conductive lines or regions, and the sensor can be used to measure static shear forces applied to the sensor.

In yet another embodiment, the present invention includes a method of designing an object or device comprising the steps of applying at least one flexible, compliant sensors capable of simultaneously measuring both shear and normal forces, to locations on a prototype design of an object or device being designed; using the prototype design with the applied sensors in at least one application or test over a test period of time; measuring both the shear and the normal forces encountered at the sensor locations of the prototype design over at least part of the test time period; and modifying the design of the object or device in part based on the forces encountered by the prototype design during the application or test.

In yet still another embodiment, the present invention includes a method of designing an object or device comprising the steps of applying at least one flexible, compliant sensors capable of measuring static shear forces, to locations on a prototype design of an object or device being designed; using the prototype design with the applied sensors in at least one application or test over a test period of time; measuring the shear forces encountered at the sensor locations of the prototype design over at least part of the test time period; and modifying the design of the object or device in part based on the forces encountered by the prototype design during the application or test.

The sensors of the present invention are preferably capable of simultaneously measure both normal and shear forces applied to the sensor. As used in this application, this further includes sensors which are capable of producing signals capable of differentiating both types of forces or combinations thereof. Preferably, the sensor of the present invention is capable to determining the three directional components of a force applied to the sensor. The sensors of the present invention are further preferably statically responsive, and more preferably statically responsive to shear forces. This means when a force, applied to the sensor, is not removed (kept static), the sensor is still responsive and puts out a signal to represent such a force.

The sensors of present invention are preferably formed from a composite sheet material having an upper and a lower surface comprising an elastomeric matrix which is essentially non-conductive, and discrete electrically conductive elements within the matrix wherein the electrically conductive elements in a region of the composite sheet material are arranged into columns, and the orientation of these columns are in an essentially organized, non-random pattern with a majority of these columns oriented at angles less than about 90° and greater than about 15° to the lower surface of the composite sheet material. The sensor, however, can be formed from other materials currently known by those skilled in the art or subsequently found useful by those skilled in the art.

The composite sheet material comprises a matrix and electrically conductive elements, and preferably comprises an elastomeric matrix and electrically conductive elements. The matrix being essentially non-conductive. Preferably, the matrix is a material that substantially recovers its original shape and size after removal of a deforming force. By way of example but not limitation, the matrix can be formed from materials including silicone rubbers, rubbers, thermoplastic polyurethanes, and other resins and combinations of those resins know to those skilled in the art. Also preferably, the elastomeric matrix is essentially non-conducting. By essentially non-conducting, it is meant that the matrix can be non-conductive, weakly conductive or semi-conductive, however, preferably the matrix is non-conductive. Preferably, the sensor is flexible, and compliant to the surface upon which it is placed. More preferably, the sensor is elastomeric. Still more preferably, the matrix has a tensile modulus @ 100% elongation of less than about 5000 psi, more preferably less than about 1500 psi, still more preferably less than about 1000 psi, and most preferably less than about 500 psi.

The electrically conductive elements within the matrix material of the present invention include but are not limited to particles, and asicular or rod like structures of nickel, iron, cobalt, copper, silver, alloys thereof, and ferrites. Also included are particles that are only conductive on their surface including any type of non-conductive or essentially non-conducting material that has been coated with a conductive coating. Most preferably, the electrically conductive elements of the present invention are a nickel-silver alloy. Examples of conductive coatings include but are not limited to metals such as silver, gold, platinum, and copper. The electrically conductive elements within the matrix material preferably are from about 0.01 to about 50 percent by volume of the composite material, more preferably from about 0.5 to about 30 percent by volume of the composite material and most preferably from about 1 to about 20 percent by volume of the composite material. While the elements can be of any shape such as irregularly and regularly shaped particles, flakes and rods, preferably the particles are spherical or near spherical in shape. Further preferably, the particle diameters are in a range from about 0.1 to about 2000 micrometers, more preferably from about 1 to about 1000 micrometers, and most preferably from about 10 to about 500 micrometers.

In one embodiment of the present invention, the composite sheet material is produced by molding a matrix material, which is essentially non-conducting and contains electrically conductive elements in a mold, such as the mold shown in FIG. 1. Preferably the thickness of the composite sheet material is from about 10 to about 5000 micrometers, more preferably from about 100 to about 2000 micrometers, and most preferably from about 100 to about 1000 micrometers. In molding the composite sheet material, preferably the material described above is fed in a fluidic uncured state into a mold 10. FIG. 1. shows an end view 12 of the mold 10, shows a top view 14 of the mold 10, and shows a side view 16 of the mold 10. The material in the mold 10 is subjected to a very large and uniform electromagnetic field 18 represented by the arrows in FIG. 1. The magnetic flux lines of this field 18 are used to align the free flowing electrically conductive elements to into columns aligned parallel to the electromagnetic field 18. The composite sheet material is then cured or the temperature is reduced in order to set the alignment of the electrically conductive elements. Depending on the curved region or curvature 20 (one section 26 being identified in FIG. 1) of the mold, this process can be used to produce a sheet material which when flattened in the curved region 20 produces a range of angles of the columns of electrically conductive elements to the upper and lower surfaces of the composite sheet material. The shape of the mold 10 is designed such that the composite sheet material is the inverse relationship of the desired aligned electrically conductive elements in the composite sheet material. One of the attributes of this invention is the design of a process which allows the electrically conductive elements in the composite sheet material to be set or cured in a non-linear orientation rather than attempting to change the electromagnetic field into a non-linear field.

In designing the mold 10 in FIG. 1, one of the preferred embodiments is to have a linear change in alignment of the electrically conductive elements or columns with respect to the location of the column in the composite sheet material. To do so, a mold 10 is preferably designed where starting at the center, the columns are aligned perpendicularly to the bottom surface of the composite sheet material, and for each given distance x to each side, the angle of the corresponding column is some factor m times that x distance. While omitting the associated analysis, preferably the mold is designed in the shape of a half-circle 20. The mold 10 is preferably designed with a "pill" shaped 24 longitudinal profile shown in FIG. 1. Additionally, preferably a "moat" 22 is designed into the mold 10 as shown in FIG. 1 to accommodate spillover during molding.

It is envisioned that other processes could be used to process the composite sheet material of the present invention. Those include variations of the processes described in U.S. Pat. Nos. 4,778,635; 4,923,739; 5,045,249; and 5,313,840, which are herein incorporated by reference, but are not limited to variations of those processes. The variations of these processes include using the manufacturing techniques described in those patents with a magnetic field with angularly varying flux lines. This would, however, not be the preferred method since producing this non-uniform type of magnetic field would be both very difficult and expensive. Another process, which can be used is to create such a composite sheet material by alternatively winding thin flexible materials and thin electrically conductive wire around a mandrel to create a similar composite sheet material with the electrically conductive elements aligned in a similar fashion.

Figure 2:
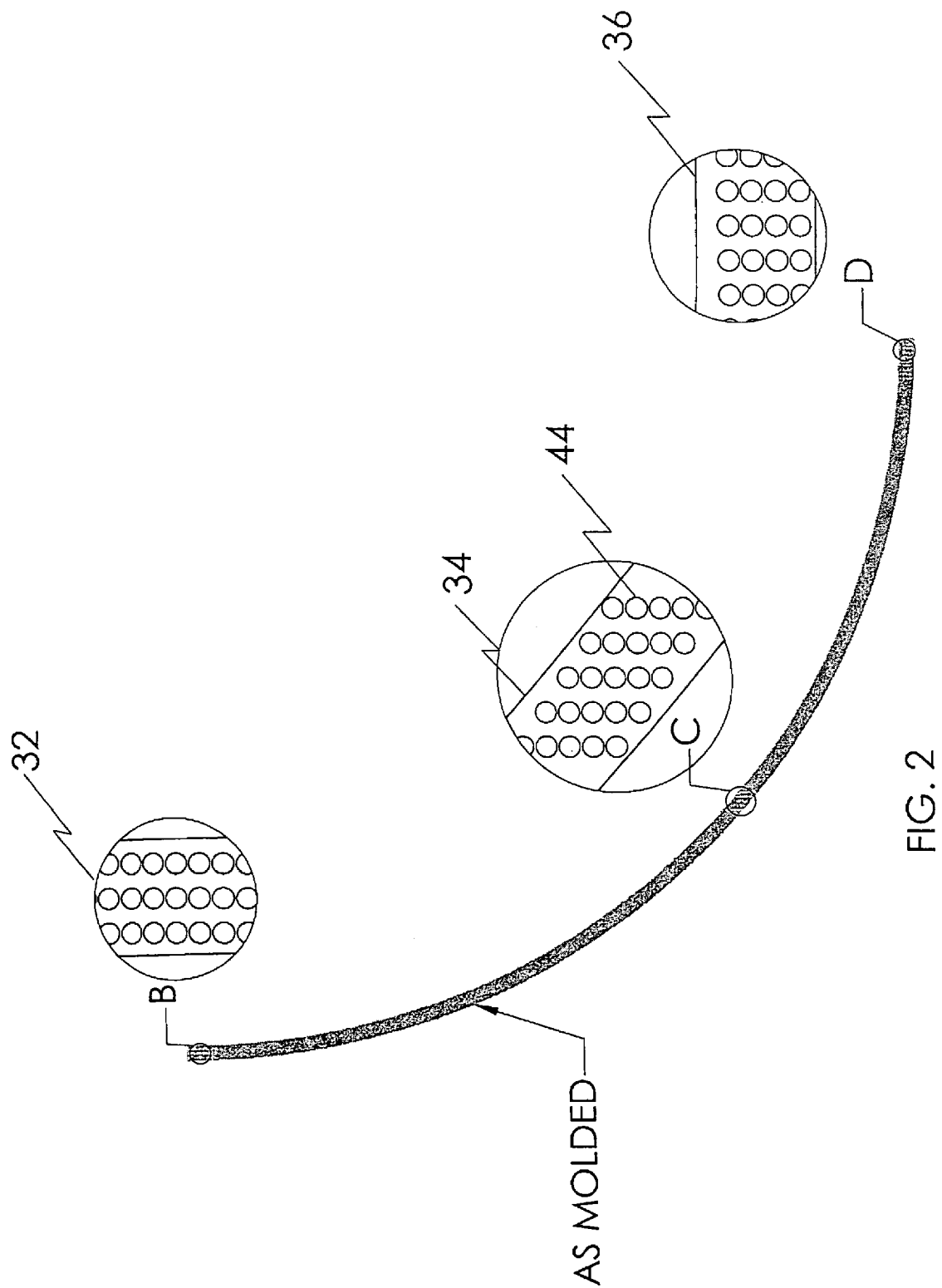
FIG. 2. Schematic representation showing the alignment of elements in section A of the composite material as molded according to FIG. 1; and further schematic representation more specifically showing the detail of the element alignment in the composite material of the sub-sections B, C and D as shown.

FIG. 2. is a schematic representation of a cross-section of section 26 identified in FIG. 1. Three sub-sections B 32, C 34, and D 36 are identified in FIG. 2. FIG. 2. further shows in greater detail the alignment of the electrically conducting elements in the composite sheet material. In the particular embodiment represented by sub-sections B, C, and D the electrically conducting elements are spherical in shape and have been aligned parallel to the magnetic field applied as represented in FIG. 1.

FIG. 3 is a schematic representation of the composite material shown in FIG. 2 after the step of flattening of the composite material, and FIG. 3. is a more detailed representation of the alignment of the electrically conducting elements 42 across the flattened composite sheet material 40. The composite sheet material 40 in some embodiments of the present invention can be flattened just by removing the material from the mold and placing it on a surface through gravity (if the composite material is thin and flexible). However, in other embodiments using a more stiff, less pliable composite material, the composite material can be flattened by methods know to those skilled in the art including the use of heat and/or pressure. It should be noted that when such composite sheet materials are processed by additional application of heat and pressure, preferably care should be taken not to significantly disturb the orientation or alignment of the electrically conducting elements in the composite material. FIG. 3 further shows a composite sheet material 40 wherein the electrically conductive elements 42 in a region, in this example section A 26 from FIG. 1, of the composite sheet material are arranged into columns 44, and the orientation of these columns are in an essentially organized, non-random pattern with a majority of the columns 44 oriented at angles 46 less than about 90° and greater than about 15° to the lower surface of the composite sheet material.

Figure 4A:
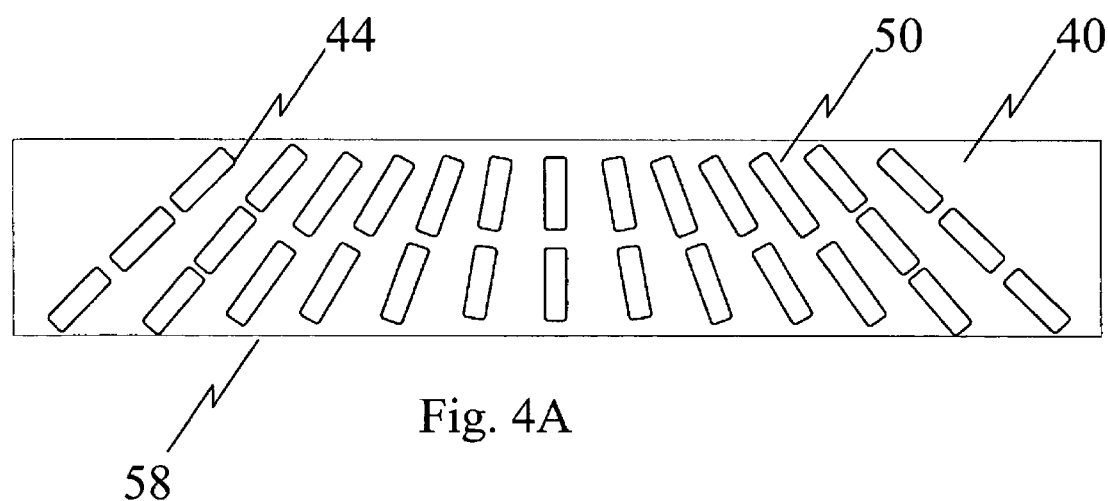
FIG. 4. A) Schematic representation of a cross section of the sub-sections of a composite material similar to the composite material show in FIG. 3 but using rod-like electrically conductive elements; and B) Schematic representation of a cross section of a composite material using a spun wire/laminating process for producing the composite material.
Figure 4B:
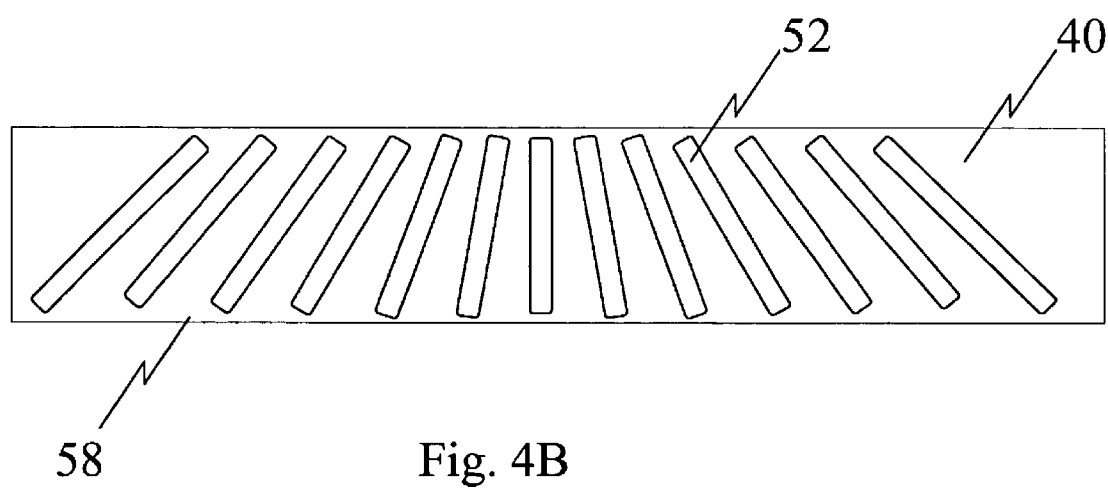

FIG. 4. A) is a schematic representation of a cross section of the sub-sections of a composite sheet material 40 similar to the composite sheet material 40 shown in FIG. 3. but using rod-like electrically conductive elements 50 described above. The rod-like electrically conductive elements 50 are aligned into columns in an essentially organized, non-random pattern with a majority of columns 44 oriented at angles less than about 90° and greater than about 15° to the lower 58 surface of the composite sheet material 40. FIG. 4B) is a schematic representation of a cross section of a composite material using a process whereby individual electrically conductive elements span at least 50%, but more preferred at least 75%, or most preferred at least 90% of the material thickness, including but not limited to a spun wire/laminating process described above for producing the composite sheet material 40. The composite sheet material 40 having individual electrical elements 52 functioning as aligned columns 44, the majority being oriented at a range of angles less than about 90° and greater than about 15° to the lower 58 surface of the composite sheet material 40. FIG. 4. represents just two of the possible embodiments for alternative electrically conductive elements and processes which can be used to produce the materials and sensors of the present invention.

Figure 5:
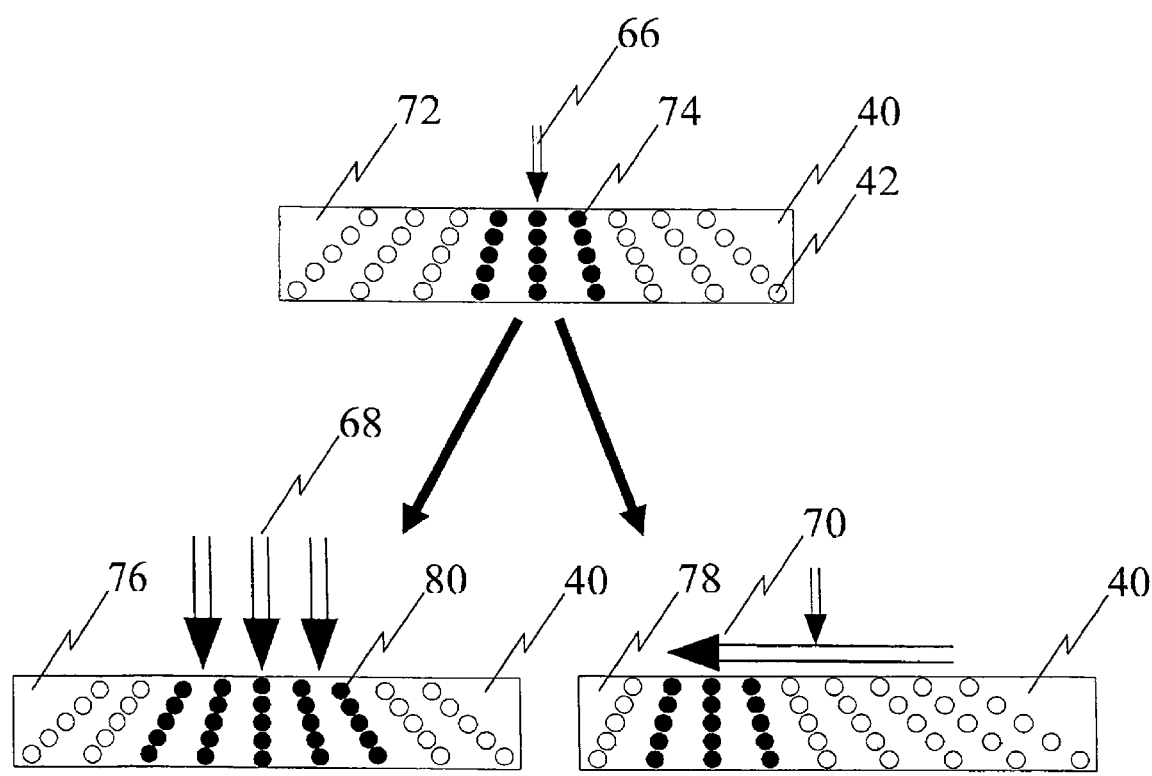
FIG. 5. Schematic representation of the composite material of the present invention under both normal and lateral forces.

Another unique feature of a number of embodiments of the present invention is represented in the schematic shown in FIG. 5. This unique feature is the ability of the sensor to measure both normal and shear forces at the same time. FIG. 5. is a schematic representation of the behavior of the electrically conductive elements 42 in the composite sheet material 40 of the present invention under both normal 66, 68 and/or lateral forces 70. Under a normal force 66, the matrix material 72 about the electrically conductive elements 42 in the composite sheet material 40 is compressed resulting in the electrically conductive elements in that region of the sensor being in contact, whereby contact is defined as electrically connected and not necessarily physically touching, with each other (those columns where the electrically conductive elements are in contact with each other being represented by the black columns of electrically conductive elements 74 in the schematic). The composite sheet material under an additional normal force 68 results in additional columns 80 of electrically conductive elements coming into contact with each other as a result of the larger normal force 68 being translated across the composite sheet material 40. The composite sheet material when under both a normal force and a shear force 78 results in a shift, in the direction of the shear or lateral force, of the columns of electrically conductive elements, which come into contact with each other.

Figure 6A:
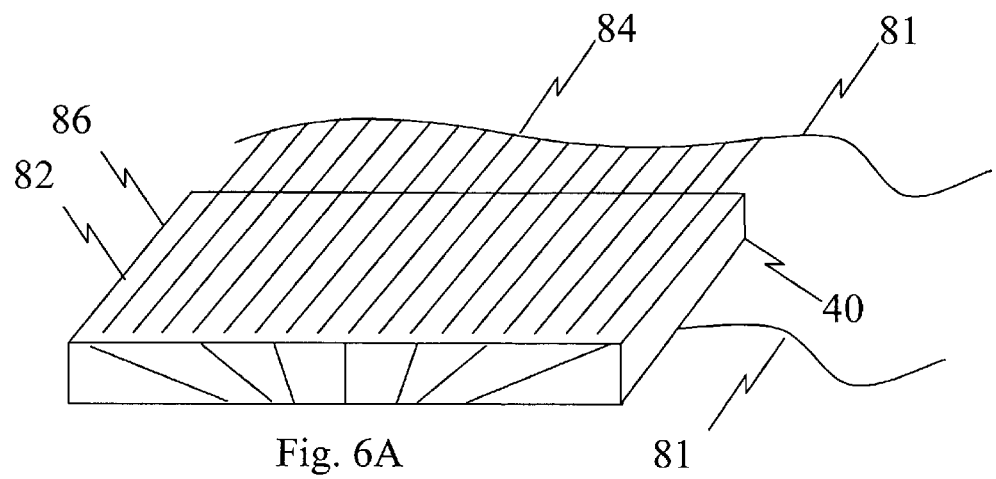
FIG. 6. Perspective view of a sensor comprising the composite material of the present invention, and two conductive elements wherein A) one of the conductive elements is a multilane element, B) one of the conductive elements is formed into two triangular shaped patterns, and C) one of the conductive elements is formed into two irregularly shaped triangular patterns.
Figure 6B:
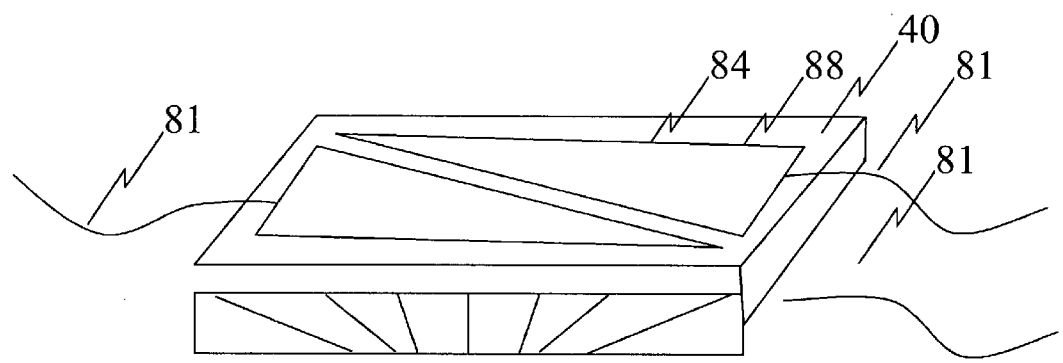
Figure 6C:
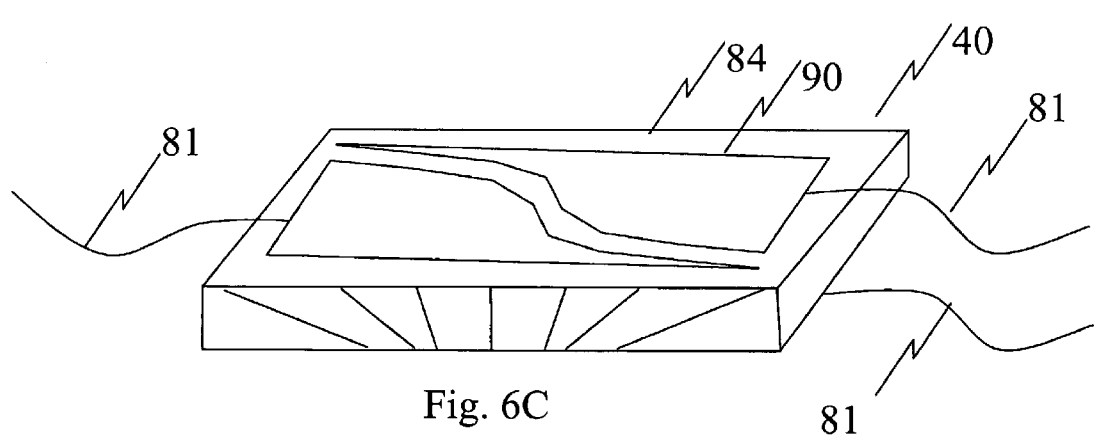

FIG. 6. are three perspective views of different embodiments of a sensor comprising the composite sheet material of the present invention. The sensor 86 comprising at least two electrical pathways 81 leading to and from a laminate material 82, and the laminate material 82 comprising two layers of contact material (or conductive elements), i.e., an upper layer 84 and a lower layer (not shown). The upper layer 84 (or conductive element) is formed from multiple conductive lines, see FIG. 6A) across the top surface of the laminate, and the lower layer preferably formed from a solid conductive layer. The upper layer 84 and lower layer being printed with conductive ink or by some other technique know to those skilled in the art on the respective surface of the composite sheet material 40. FIG. 6B) is another embodiment of the sensor 86 described above except that the upper layer 84 (or conductive element) is formed by two conductive triangular patterns 88 on the upper surface of the composite sheet material 40. FIG. 6C) is still another embodiment of the sensor 86 described above except that the upper layer 84 (or conductive element) is formed by two irregular conductive triangular patterns 90 on the upper surface 84 of the composite sheet material 40.

Figure 7A:
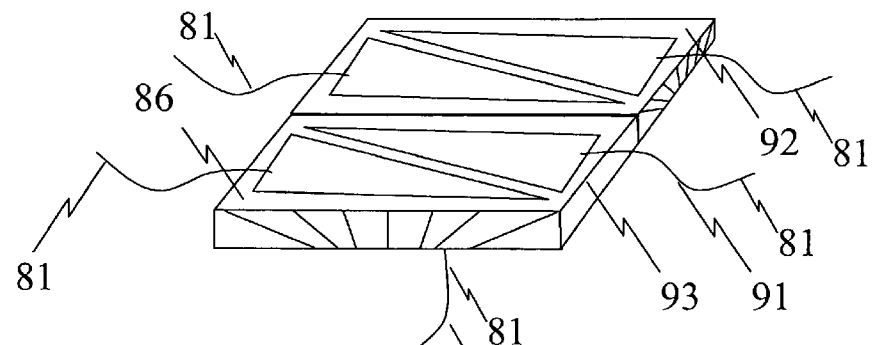
FIG. 7. A, B) Perpective view of two sensors, which can be used to measure lateral forces over 360° in a plane; and C) Exploded view of a single sensor, which can be used to measure lateral forces over 360° in a plane.
Figure 7B:
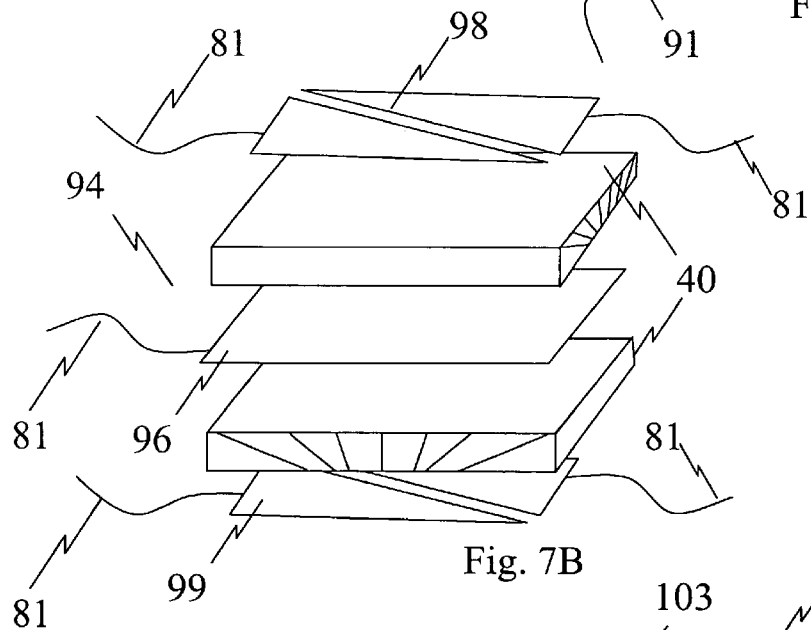
Figure 7C:
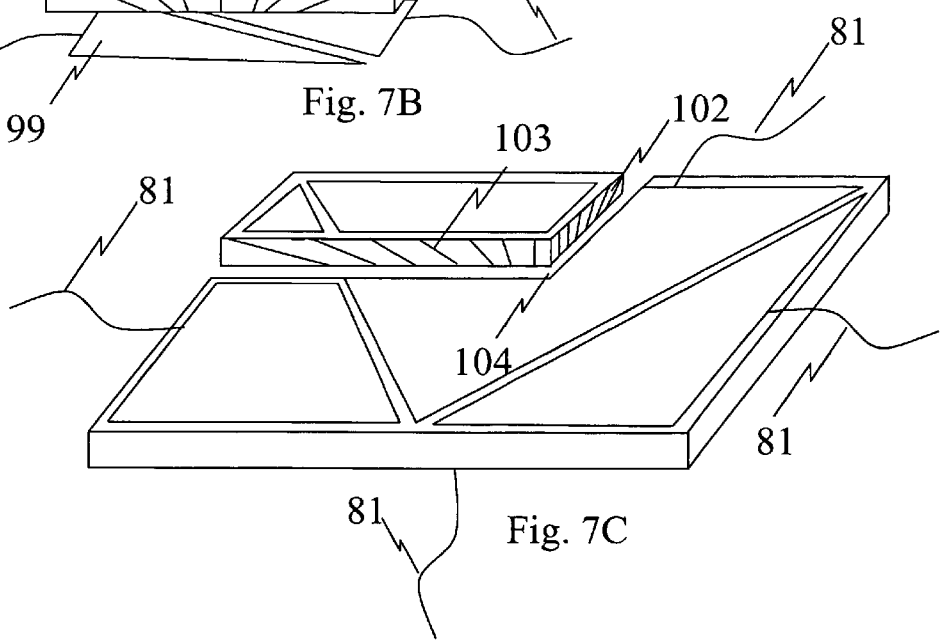

FIG. 7. represents several embodiments of an overall sensor 92 required to measure stress or forces in all directions. FIG. 7. shows a sensor comprising at least two electrical pathways 91 to or from a laminate material 93. FIG. 7A) is a sensor 92 comprised of two of the sensors 86 shown in FIG. 6. In FIG. 7A) two of the sensors 86 shown in FIG. 6 are placed side by side and formed into a sensor 92 which can measure both normal as well as shear (or lateral) forces in all directions. FIG. 7B) is a different configuration of such a sensor 92. In FIG. 7 B) a laminate 94 is formed by stacking two layers of composite sheet material 40 about a conductive sheet layer (or contact material) 96 and then applying both upper 98 and lower 99 surfaces of contact material in patterns similar to those described for the upper surface in FIG. 6B). Of course, the contact material for the upper 98 and lower 99 surfaces of this laminate could have patterns similar to those described in FIGS. 6A) and C) or of a pattern known to those skilled in the art which would function equivalently. FIG. 7C) is still a different configuration of a sensor 92 which can measure both normal and lateral (shear) forces. In FIG. 7C) the composite sheet material 102 is comprised of a composite material wherein the columns of electrically conductive elements 103 radiate from about the center 104 of the composite sheet material.

Figure 8:
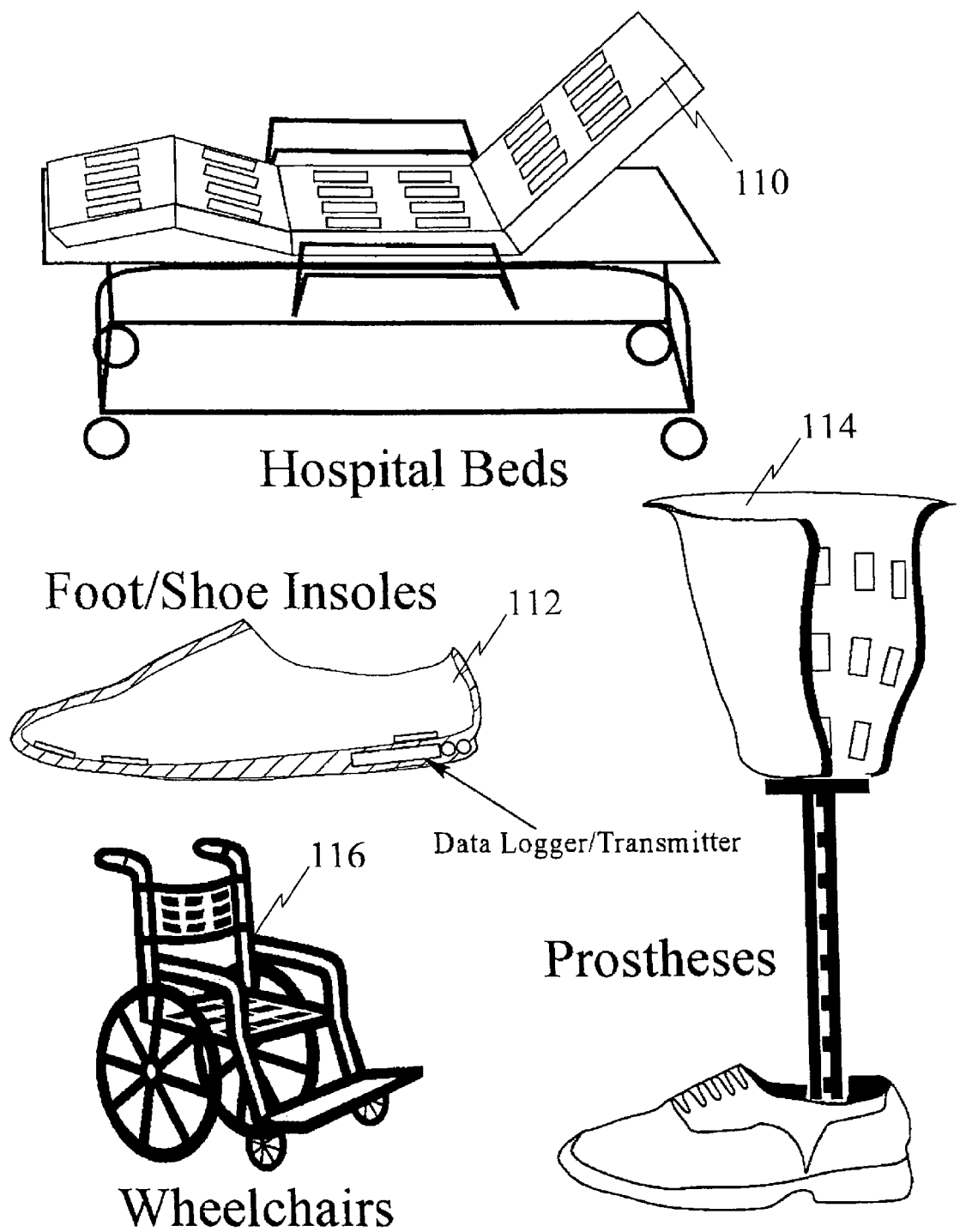
FIG. 8. Schematic representation demonstrating typical applications of the sensor.

FIG. 8 shows the sensors of the present invention in a number of applications. For medical applications, the sensors can be used in hospital beds 110 or mattresses 110, in shoes or athletic footwear 112, on prostheses 114 or in wheel chairs 116. Furthermore, the sensor of the present invention has application anywhere it would be helpful to measure shear and/or normal forces a person, a device or an article might undergo. The sensor of the present invention would be helpful in designing any object or devices which undergo a series of shear and/or normal forces during regular use of the object or device. By better understanding these shear and/or normal forces, changes can be made in the object or device to improve the performance for the user. One method of using the sensors of the present invention in designing an object or device has a number of steps. The first step is to apply at least two, flexible compliant sensors capable of simultaneously measuring both shear and normal forces to locations on a prototype or existing design of an object being designed. In particular, it would be helpful to place the sensors in locations particularly prone to the largest shear and/or normal forces during use or application. The prototype is then to be used in a typical application, or under certain desired test conditions over a certain test time period. The prototype can be a newly designed object or device, or an existing object or device to which improvement is hoped to be made. During the test time period, both the shear and normal forces encountered at the sensor locations are measured. The design of the object or device is then modified in part based on the measured forces encountered by the prototype in the typical application or under those specific testing conditions.

A specific example of the method described above would be the use of these types of sensors in the design of athletic footwear. In designing athletic footwear, sensors of the present invention (or other sensors developed at a later date by those skilled in the art which can measure both shear and normal forces) are placed in locations on one or more articles of footwear at locations where it is desirable to better understand the forces encountered by a person wearing the footwear or to better understand the forces encountered under certain conditions. The footwear is used in a typical application (such as being worn by a test subject in an athletic event, e.g., basketball game, hockey game, baseball game, football game, soccer game, etc.) by a person, or is machine tested under specific testing conditions over a test time period. The test time period is that period of time over which data about the forces encountered in an application or under specific testing conditions is gathered, which is necessary for a person skilled in the art to understand so as to modify or re-design the object or device, i.e., the athletic footwear. During at least part of the test period, the shear and normal forces encountered at the sensor locations in the athletic footwear is measured, and the measurement data is used at least in part to modify or re-design the athletic footwear. It is understood that many factors take place in the design of objects, articles or devices, some of the factors being more subjective such as appearance, etc, but the present invention provides a method of design which takes into account the physical factors encountered by an object, article or device and allows for a re-design or modification which reduces the effect of these physical factors on the user, or reduces the magnitude of these physical factors on the object, article, or design themselves.

The sensors can be used to design or in medical devices, footwear including athletic footwear, consumer goods, manufacturing equipment, robotics, for processing, in household furnishings, and in the design or in any type of object or device known to someone skilled in the art. The sensors can be used to design or in everyday applications, consumer applications, in medical applications including uses by patients, consumer applications, and in any other applications know to those skilled in the art.

Figure 9:
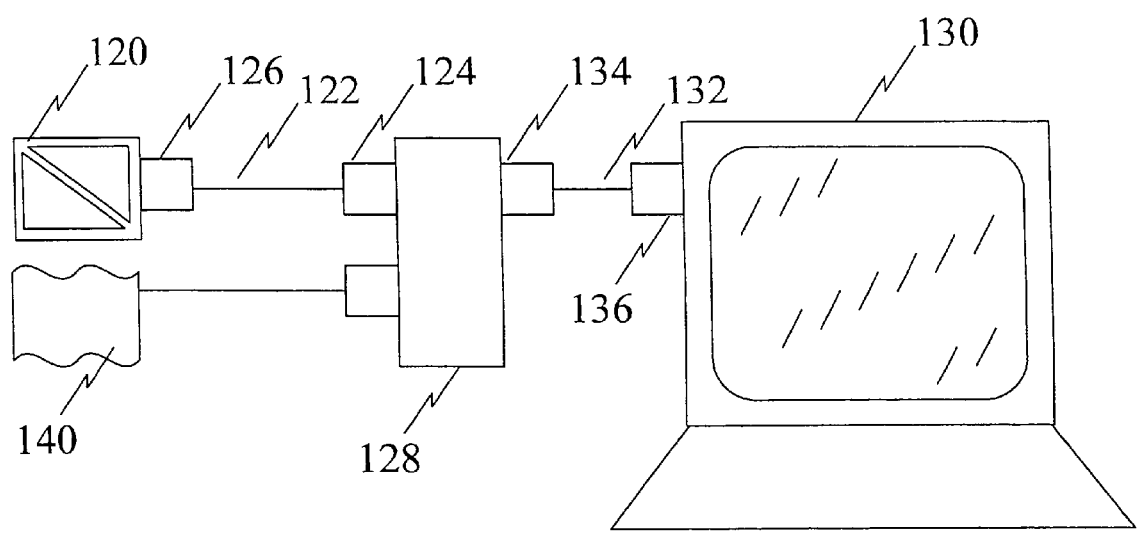
FIG. 9. Schematic representation of one embodiment of the sensor and related electronics of the present invention.

The present invention further includes a system which includes a sensor described herein wherein the sensor is combined with a closed loop control system to activate an actuator in response to certain sensor signals. FIG. 9. is a schematic representation of one embodiment of the sensor and related electronics of the present invention. The sensor 120 responds according to the forces exerted against the sensor. The sensor 120 is placed at a probable high pressure point, for instance, under the seat cushion on a wheelchair of a paraplegic at points where the ischial tuberosity, coccyx and/or trochanter locate when a paraplegic is seated on the wheelchair. For a diabetic it can be located on the heal, hallux or metatarsal heads. Advantageously, multiple sensors 120 may be used. It is not necessary that the sensor 120 be in actual contact with the skin of a person for it to adequately respond to a pressure exerted on the skin. The sensor 120 can be embedded within an object or device without significantly affecting its operation. This is accomplished by properly calibrating the sensor 120 to allow for force distributions through the device the sensor is embedded into. The sensor 120 sends multiple signals corresponding to the normal and/or shear forces exerted on the sensor 120 to a microcontroller (not shown) by way of the sensor lead(s) 122 (or electrical pathway(s)). In this embodiment, the sensor lead 122 terminates at one end with a sensor connector 124 for connection to the controller housing 128. The lead connector 126 can be optionally added to reduce the size of the sensor 120 thereby reducing the cost when the sensor 120 needs to be replaced. In other embodiments, two or more sensors 120 can be used in which case the sensor connector 124 can be any suitable connector know to those skilled in the art. A controller 130, such as a personal computer, connects to the controller housing by way of interface cable 132. Advantageously, interface cable 132 is optically coupled, electronically isolated data cable. The interface cable 132 terminates at one end in a cable plug 134, which can be a miniature phone plug, for connection to the controller housing 128 and at the other end in an isolating connector 136 for connection with the personal computer or controller for programming. The personal computer can be used to collect and/or analyze the data, or to activate an actuator 140.

Figure 10:
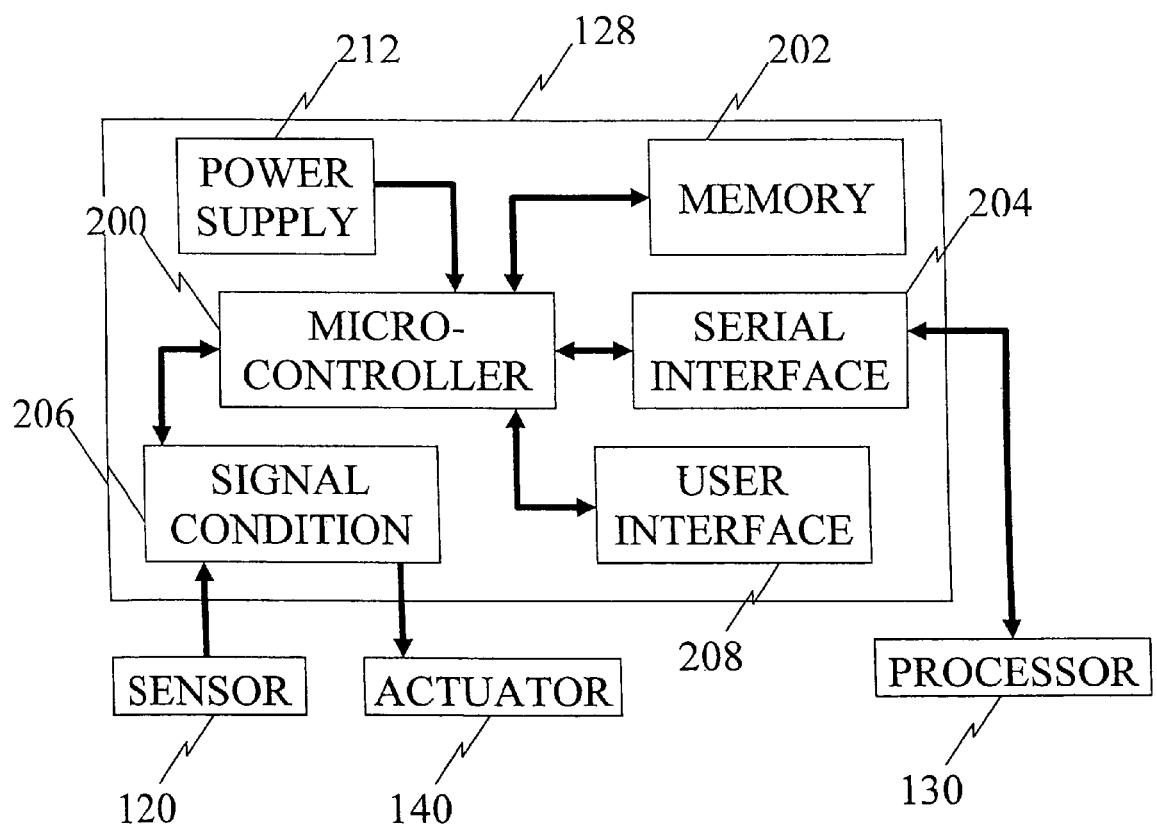
FIG. 10. Block diagram demonstrating another embodiment of the present invention.

FIG. 10. is a block diagram of one embodiment of the present invention. The microcontroller 200, non-volatile memory 202, serial interface 204, signal conditioning filter 206, and user interface 208 are located in the controller housing 128. The microcontroller 200 controls the device executing monitoring algorithms, periodic sampling of the sensor 120, generating signals to an actuator, and recording events of interest. A non-volatile memory 202 maintains a complete record of events and stores values for the level and duration of both normal and/or shear forces, and the duration of the relief from pressure, which were programmed therein. The signal conditioning filter 206 may include one or more operational amplifiers (not shown). The operational amplifier provides electrical isolation between the sensor(s) 120 and the other components, thus providing additional safety for the user by reducing the hazard of electrical shock.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of designing an object or device comprising the steps of:
    applying at least one flexible, compliant sensor capable of measuring static shear forces to locations on a prototype design of an object or device being designed;
    using the prototype design with the applied sensor in at least one application or test over a period of time; and
    modifying the design of the object or device in part based on the measured shear forces encountered by the prototype design during the application or test.

2. The method in claim 1, wherein the object or device is a medical device.

3. The method in claim 2, wherein the application is use by a patient.

4. The method in claim 1, wherein the object or device is athletic footwear and the test over the period of time comprises testing the athletic footwear on a test machine.

5. The method in claim 1, wherein the flexible, compliant sensor capable of measuring static shear forces comprises two conductive element layers and a flexible material interposed between and in contact with the two conductive element layers, and wherein the flexible material interposed between and in contact with the two conductive element layers comprises an elastomeric matrix which is essentially non-conductive and discrete electrically conductive elements within the elastomeric matrix.

6. The method in claim 5, wherein the discrete electrically conductive elements within the elastomeric matrix are arranged into columns oriented at less than about 90° and greater than about 15° to the lower conductive element layer.

7. The method in claim 5, wherein the discrete electrically conductive elements comprise rod-like structures of nickel, iron, cobalt, silver, ferrites, or alloys thereof.

8. The method in claim 1, wherein the object or device is an automobile.

9. The method in claim 1, wherein the object or device is a household furnishing.

10. The method in claim 1, wherein the application is aviation.

11. The method of claim 1, further including the step of receiving with a data logger or transmitter located on or embedded in the object or device a signal from the at least one sensor used to measure the shear forces.

12. The method of claim 11, further including the step of transmitting the signal with the transmitter to a computer separate from the object or device for storing or analyzing the signal from the sensor.

13. The method of claim 1 wherein the flexible, compliant sensor is also capable of measuring normal forces.

14. The method of claim 1, wherein the sensor is placed in a location on the object or device prone to the largest shear forces during use or application.

15. The method of claim 1, further including a step of receiving with a controller a signal from the at least one sensor used to measure the shear forces and a step of activating an actuator with the controller based on at least in part the signal from the at least one sensor.

16. A method of designing an object or device comprising the steps of:
    (a) applying at least one flexible, compliant sensor to locations on a prototype design of an object or device being designed, the sensor comprising:
        two conductive element layers, and
        a flexible material interposed between and in contact with the two conductive element layers,
        wherein the sensor is capable of simultaneously measuring both shear and normal forces applied to the sensor;
    (b) using the prototype design with the applied sensor in at least one application or test over a period of time;
    (c) measuring both the shear and normal forces encountered at the sensor locations of the prototype design over at least part of the test time period; and
    (d) modifying the design of the object or device in part based on the forces encountered by the prototype design during the application or test.

17. The method in claim 16, wherein the object or device is a medical device.

18. The method in claim 16, wherein the flexible material interposed between and in contact with the two conductive element layers comprises an, elastomeric matrix which is essentially non-conductive and discrete electrically conductive elements within the elastomeric matrix.

19. The method in claim 18, wherein the discrete electrically conductive elements within the elastomeric matrix are arranged into columns oriented at less than about 90° and greater than about 15° to the lower conductive element layer.

20. The method in claim 18, wherein the discrete electrically conductive elements within the elastomeric matrix comprise a nonconductive material that has been coated with a conductive coating.

21. The method of claim 18, wherein the discrete electrically conductive elements within the elastomeric matrix comprise rod-like structures of nickel, iron, cobalt, silver, ferrites, or alloys thereof.

22. The method in claim 16, wherein the object or device is an automobile.

23. The method in claim 16, wherein the object or device is a medical device.

24. A method of designing an object or device comprising the steps of:
    (a) applying at least one flexible, compliant sensor capable of simultaneously measuring both shear and normal forces to locations on a prototype design of an object or device being designed;
    (b) using the prototype design with the applied sensor in at least one application or test over a period of time;
    (c) measuring both the shear and normal forces encountered at the sensor locations of the prototype design over at least part of the test time period; and
    (d) modifying the design of the object or device in part based on the forces encountered by the prototype design during the application or test.

25. The method in claim 24, wherein the object or device is athletic footwear and the test over the period of time comprises testing the athletic footwear on a test machine.

26. The method in claim 24, wherein the object or device is an automobile.

27. The method of claim 24, further including the step of receiving with a data logger or transmitter located on or embedded in the object or device a signal from the at least one sensor used to measure the shear and normal forces.

28. The method of claim 27, further including the step of transmitting the signal with the transmitter to a computer separate from the object or device for storing or analyzing the signal from the sensor.

29. The method of claim 24, wherein the sensor is placed in a location on the object or device prone to the largest shear and/or normal forces during use or application.

* * * * *